United States Patent [19]

Hagedorn

[11] Patent Number: 4,673,646

[45] Date of Patent: * Jun. 16, 1987

[54] PRODUCTION OF 2-HYDROXYMUCONIC SEMIALDEHYDE

[75] Inventor: Scott Hagedorn, Summit, N.J.

[73] Assignee: Celanese Corporation, New York, N.Y.

[*] Notice: The portion of the term of this patent subsequent to Mar. 31, 2004 has been disclaimed.

[21] Appl. No.: 764,768

[22] Filed: Aug. 12, 1985

Related U.S. Application Data

[62] Division of Ser. No. 582,237, Feb. 22, 1984, Pat. No. 4,617,156.

[51] Int. Cl.$^4$ .................. C12P 7/42; C12N 15/00; C12N 1/20; C12R 1/40
[52] U.S. Cl. .................. 435/146; 435/172.3; 435/253; 435/877
[58] Field of Search .............. 435/172.3, 68, 317, 435/253, 877, 136, 122, 146, 142, 172.1

[56] References Cited

PUBLICATIONS

Davis et al 1968 "Metabolism of p- and m-xylene by Species of Pseudomonas" *Can. J. Micro.* v14 1005–9.

*Primary Examiner*—Thomas G. Wiseman
*Assistant Examiner*—Joanne Giesser
*Attorney, Agent, or Firm*—Depaoli & O'Brien

[57] ABSTRACT

This invention provides a process for the bioconversion of a non-growth aromatic feed to an accumulated quantity of 2-hydroxymuconic semialdehyde metabolite.

2-Hydroxysemialdehyde is a useful intermediate for subsequent conversions to picolinic acid and pyridine.

12 Claims, No Drawings

PRODUCTION OF 2-HYDROXYMUCONIC SEMIALDEHYDE

This is a continuation, of application Ser. No. 582,237 filed 2/22/84, U.S. Pat. No. 4,617,156.

BACKGROUND OF THE INVENTION

Heterocyclic compounds such as pyridine currently are recovered as constituents of coal tar, or are synthesized for example by the reaction of acetaldehyde with ammonia and formaldehyde to provide a pyridine, alpha-picoline and beta-picoline product mixture. Specialty heterocyclic aromatic chemicals are utilized in the production of adhesives, pesticides, vitamins, and the like.

Another prospective route to heterocyclic aromatic compounds is by the reaction of ammonia or a primary amine with a 2-hydroxymuconic semialdehyde to form a picolinic acid:

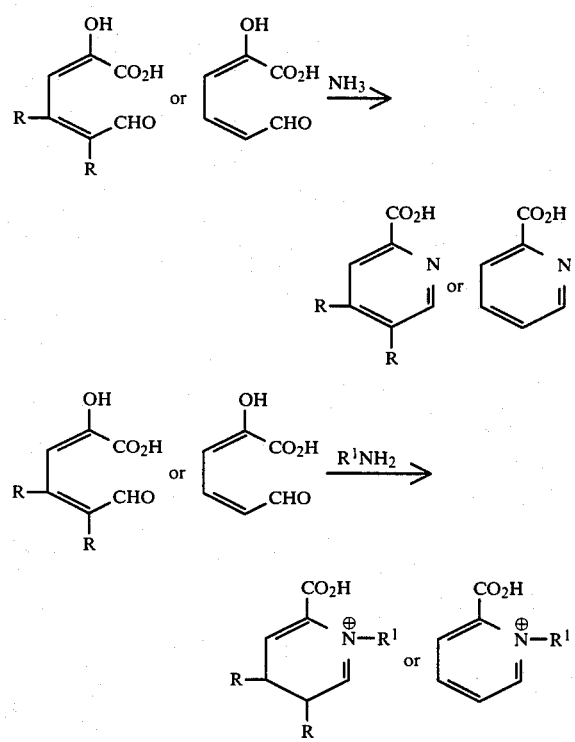

Subsequent decarboxylation of the picolinic acid could provide the corresponding pyridines and substituted pyridines, as illustrated in the Journal of Organic Chemistry, 37(24), 3938(1972) article by R. J. Moser et al.

A potentially convenient source of 2-hydroxymuconic semialdehyde is by the microbiological oxidation of various hydrocarbon substrates. Microbiological oxidation of aromatic substrates is reviewed by S. Dagley in Advances in Microbial Physiology, 6, 1–47(1971); by P. Chapman in Degradation Of Synthetic Organic Molecules In The Biosphere, pages 17–55, National Academy Of Sciences, 1972; and by P. Williams in "Microbial Degradation Of Xenobiotics And Recalcitrant Compounds", pages 97–107, Academic Press, 1981. Strains of microorganisms are known which metabolize aromatic hydrocarbon substrates by the meta pathway via catechol and 2-hydroxymuconic semialdehyde to biomass and carbon dioxide.

The Nature, 188, 560(1960) article by S. Dagley et al describes the cleavage of catechol by a solution of an enzyme, catechol 2,3-oxygenase, to produce a product with a yellow color in the bioconversion medium. The ultraviolet absorption spectrum indicates a 2-hydroxymuconic semialdehyde type product, which on standing with ammonium hydroxide forms alpha-picolinic acid.

The Canadian Journal of Microbiology, 14 1005(1968) article by R. S. Davis et al describes the metabolism of p-xylene and m-xylene by species of Pseudomonas. A metabolite is produced by a solution of enzyme which has an ultraviolet spectrum consistent with a 2-hydroxymuconic semialdehyde structure. A solution of this metabolite treated with ammonium hydroxide yields a picolinic acid type product.

The Biochemical Journal, 106, 859(1968) publication by R. B. Cain et al also describes the formation of 5-methylpicolinic acid from 4-methylcatechol via 2-hydroxy-5methylmuconic semialdehyde, utilizing a cell extract prepared from a microorganism grown on toluene sulfonate.

The Journal of Bacteriology, 120(1), 31(1974) publication by G. J. Wigmore et al describes Pseudomonas putida mutants which metabolize phenol and cresols by the meta pathway via catechol and 2-hydroxymuconic semialdehyde intermediates. One mutant strain is described as being defective in both 2-hydroxymuconic semialdehyde hydrolase and dehydrogenase.

The potential of microbiological oxidation of an mutant strains of microorganisms which (1) metabolize an aromatic substrate such as toluene as a convenient source of 2-hydroxymuconic semialdehyde requires the construction of aromatic substrate via catechol or substituted catechol by means of the meta (catechol 2,3-oxygenase) pathway, and (2) allow the accumulation of a 2-hydroxymuconic semialdehyde type metabolite without its further assimilation to other metabolites.

Accordingly, it is an object of this invention to provide a process for the bioconversion of an aromatic hydrocarbon by the meta pathway to accumulated 2-hydroxymuconic semialdehyde or substituted 2-hydroxymuconic semialdehyde.

It is another object of this invention to provide a microbial culture which is capable of metabolizing toluene or substituted toluene, a catechol or substituted catechol, to 2-hydroxymuconic semialdehyde or substituted 2-hydroxymuconic semialdehyde metabolite quantitatively, with an accumulation greater than about 0.1 gram of metabolite per liter of bioconversion medium.

It is a further object of this invention to provide a process for the production of a picolinic acid product from an aromatic hydrocarbon via a 2-hydroxymuconic semialdehyde intermediate.

Other objects and advantages of the present invention shall become apparent from the accompanying description and examples.

DESCRIPTION OF THE INVENTION

One or more objects of the present invention are accomplished by the provision of a process for the production and accumulation of 2-hydroxymuconic semialdehyde or substituted 2-hydroxymuconic semialdehyde which comprises supplying toluene or substituted toluene and molecular oxygen to a bioconversion medium containing a microbial culture which possesses catechol 2,3-oxygenase with activity that is not inhibited in the presence of a low level of 2-hydroxymuconic semialdehyde or substituted 2-hydroxymuconic semialdehyde in a bioconversion medium, and which exhibits no enzymatic activity that metabolizes 2-hydroxymuconic semialdehyde or substituted 2-hydroxymuconic semialdehyde.

In another embodiment, this invention provides a process for the production and accumulation of a 2-hydroxymuconic semialdehyde type metabolite which comprises providing a supply of an aromatic hydrocarbon corresponding to the formula:

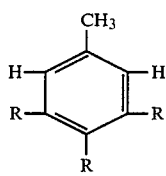

where R is hydrogen or an alkyl group containing between about 1-4 carbon atoms, and molecular oxygen to a biconversion medium containing a microbial culture of a strain which has been constructed to possess catechol 2,3-oxygenase with activity that is not inhibited in the presence of a low level (e.g., less than about 0.1 gram) of a 2-hydroxymuconic semialdehyde metabolite per liter of bioconversion medium, and which lacks active catechol 1,2-oxygenase, 2-hydroxymuconic semialdehyde hydrolase and 2-hydroxymuconic semialdehyde dehydrogenase, wherein the metabolite which is produced and accumulated corresponds to the formula:

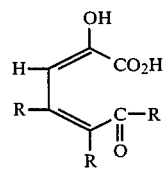

where R is as previously defined.

In another embodiment, this invention provides a process for the production and accumulation of 2-hydroxymuconic semialdehyde or substituted 2-hydroxymuconic semialdehyde which comprises supplying catechol or substituted catechol and molecular oxygen to a bioconversion medium containing a microbial culture which possesses catechol 2,3-oxygenase with activity that is not inhibited in the presence of a low level of 2-hydroxymuconic semialdehyde or substituted 2-hydroxymuconic semialdehyde in a bioconversion medium, and which exhibits no enzymatic activity that metabolizes 2-hydroxymuconic semialdehyde or substituted 2-hydroxymuconic semialdehyde.

In a further embodiment, this invention provides a novel 2-hydroxymuconic semialdehyde bisulfite adduct corresponding to the formula:

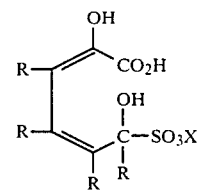

where R is hydrogen or an alkyl group containing between about 1-4 carbon atoms, and X is a cation counter-ion such as alkali metal or ammonium.

Microorganism Construction Procedures

A detailed elaboration of methods of microbe construction is disclosed in copending patent application Ser. No. 532,341, filed Sept. 15, 1983, incorporated herein by reference.

In the construction process, the starting microorganism can be any organism capable of growth on the selected aromatic substrate and possessing active catechol 2,3-oxygenase, e.g., a Pseudomonad. A variety of gram negative organisms have these traits including some members of the species *Pseudomonas putida*, *Pseudomonas aeruginosa* and *Pseudomonas fluorescens;* and some members of the genera *Azotobacter, Klebsiella* and *Serratia.*

The metabolism of toluene, m-xylene and p-xylene is performed by the enzymes of genes (Xyl A-Xyl G) normally encoded on a TOL plasmid. Toluene and p-xylene can be metabolized by either the Xyl F or Xyl G gene encoded enzymes. m-Xylene is committed to metabolism by the Xyl F gene encoded enzyme due to the inherent chemical structure of the metabolic intermediates. Toluene (but not p-xylene or m-xylene) can be metabolized by chromosomal ortho pathway enzymes, as reported by D. A. Kunz et al, Journal of Bacteriology, 146, 952(1981).

The mutant construction strategy is first to block the metabolism of benzoate on the chromosome. A wild type TOL plasmid then is introduced into the mutant microorganism. Selection is made for a mutant defective in Xyl F and unable to grow on m-xylene, but which still grows on toluene and p-xylene via the Xyl G encoded enzyme. A mutant of the Xyl F defective strain is isolated, which is mutant in Xyl G, and which allows the accumulation of 2-hydroxymuconic semialdehyde from the metabolism of an aromatic substrate such as toluene.

The growth medium consists of 91.2 mM $Na_2HPO_4$, 58.8 mM $KH_2PO_4$, 15.1 mM $(NH_4)_2SO_4$, 2.46 g/l $MgSO_4 \cdot 7H_2O$ 1.1 g/l, $CaCl_2 \cdot 6H_2O$ and 0.0268 g/l $FeSO_4$, with a ph of 7.0 (NO medium). The appropriate water soluble carbon sources are added in the range of 5-10 mM.

Growth of microorganisms on aromatic hydrocarbons in liquid cultures is achieved by adding the hydrocarbon to pre-sterilized polypropylene nitrogen storage vials and placing the vials in shake flasks. Growth of microorganisms on aromatic hydrocarbons or solid media is accomplished by adding 2% agar to the above described NO medium prior to sterilization. Hydrocarbon is provided by placing a glass vial containing the appropriate hydrocarbon in the lid of a Petri dish containing the agar minimal media.

Growth typically is measured by determining the turbidity of the cell suspension in a Klett-Summerson Colorimeter using the #66 red filter. One Klett unit is equivalent to about 3.5 mg dry weight per liter. Cultures are stored with 10 percent glycerol under liquid nitrogen.

Induction of mutants unable to grow on the hydrocarbons is accomplished by growing the culture in Luria Broth overnight with a vial of the liquid hydrocarbon.

For whole cell oxygen uptake assay, 50 ml of a cell suspension of an optical density of 200–300 klett units is centrifuged, washed and resuspended in 5.0 ml, 50 mM phosphate buffer (pH 7.9) and 0.1% antifoam. The concentrated cell suspension is oxygenated with pure oxygen for two minutes. 2.0 ml of the oxygenated cell suspension is used in a Clark oxygen electrode (Yellow Springs Instrument Co.), and the endogenous rate of oxygen uptake is recorded. 30 μl of 10 mM substrate is then added and the increased rate oxygen uptake is measured.

For preparation of cell extracts, 1.0 g of a frozen cell suspension is thawed in 2.0 ml of 50 mM phosphate buffer, pH 7.0. The thawed cell suspension is passed through a French pressure cell followed by treatment with DNase (1.0 mg) and RNase (1.0 mg) for 10 minutes at room temperature. The extract is then centrifuged at 12,000 xg for 15 min. at 5° C., and the supernatant is used for enzyme assays.

For enzyme assays 2-hydroxymuconate Semialdehyde (HMSA) is prepared using 60 nmoles of catechol in 1.0 ml of 50 mM phosphate buffer, pH 7.0, and 10–50 μl of a cell extract of toluene induced mutant (defective in Xyl G and Xyl F). The catechol is oxidized to completion as determined by no further increase in absorbance at 375 nm, and used to assay for HMSA hydrolase and HMSA dehydrogenase.

The construction procedure is adapted to provide a microbial culture which possesses active catechol 2,3-oxygenase with activity that is not inhibited in the presence of a low level of 2-hydroxymuconic semialdehyde per liter of bioconversion medium, and which lacks active muconate lactonizing enzyme, 2-hydroxymuconic semialdehyde hydrolase and 2-hydroxymuconic semialdehyde dehydrogenase.

A herein described microbial culture is capable of metabolizing an aromatic substrate selected from toluene and substituted toluene by the meta pathway via catechol or substituted catechol to 2-hydroxymuconic semialdehyde or substituted 2-hydroxymuconic semialdehyde, and it possesses catechol 2,3-oxygenase activity that is not inhibited in the presence of a low level of 2-hydroxymuconic semialdehyde or substituted 2-hydroxymuconic semialdehyde in a bioconversion medium, and it exhibits no enzymatic activity that metabolizes 2-hydroxymuconic semialdehyde or substituted 2-hydroxymuconic semialdehyde. This type of microbial culture is also capable of bio-oxidizing catechol or substituted catechol quantitatively to accumulate 2-hydroxymuconic semialdehyde or substituted 2-hydroxymuconic semialdehyde.

Illustrative of suitable microorganisms are constructed strains of microorganisms, e.g., fluorescent Pseudomonads, each of which has the following characteristics:

(a) possesses active catechol 2,3-oxygenase;
(b) lacks active muconate lactonizing enzyme;
(c) lacks active 2-hydroxymuconic semialdehyde hydrolase;
(d) lacks active 2-hydroxymuconic semialdehyde dehydrogenase; and
(e) cells are rod shaped, vigorously motile and polarly flagellated.

A novel strain of *Pseudomonas putida* Biotype A having the above recited characteristics has been deposited with the Americas Type Culture Collection and has been designated as ATCC No. 39213.

A constructed mutant strain (e.g., *Pseudomonas putida* Biotype A, strain ATCC No. 39213) has characteristics which are unique for the microbiological conversion of toluene or substituted toluene for the production and accumulation of 2-hydroxymuconic semialdehyde or substituted analog of 2-hydroxymuconic semialdehyde at a high rate and concentration.

First, the parent microorganism is capable of growing at a rapid rate, e.g., a growth doubling time of about two hours on toluene or substituted toluene.

Second, the mutant microorganism metabolizes toluene or substituted toluene by the meta pathway via catechol cleavage by the action of catechol 2,3-oxygenase. Concomitantly, no active catechol 1,2-oxygenase appears to be induced in the microorganism culture.

Third, the catechol 2,3-oxygenase activity is not repressed or inhibited by the presence of a low level of a 2-hydroxymuconic semialdehyde metabolite, e.g., a level of metabolite less than about 0.1 gram/liter in the bioconversion medium. This permits the accumulation of 2-hydroxymuconic semialdehyde at a level which is higher than about 0.1 gram/liter of medium.

Fourth, the meta pathway series of conversion reactions is blocked subsequent to the formation of the 2-hydroxymuconic semialdehyde from catechol. The mutant microorganism lacks the presence of active muconate lactonizing enzyme, 2-hydroxymuconic semialdehyde hydrolase and 2-hydroxymuconic semialdehyde dehydrogenase enzymes. Hence, the 2-hydroxymuconic semialdehyde metabolite is able to accumulate as it is produced, until the level of metabolite in the bioconversion medium inhibits the activity of the enzymes in the toluene oxidation pathway, i.e., the 2-hydroxymuconic semialdehyde metabolite accumulates up to a level of about one gram per liter of bioconversion medium. No microorganism is reported in the literature as able to produce and accumulate a 2-hydroxymuconic semialdehyde metabolite to these levels from an aromatic hydrocarbon substrate or any other aromatic substrate.

Microbial cultures described herein have an inherent genetic characteristic in common, i.e., each microbial culture is capable of biologically oxidizing toluene or catechol, or substituted toluene or catechol, quantitatively by the meta pathway to an accumulated quantity of 2-hydroxymuconic semialdehyde or substituted 2-hydroxymuconic semialdehyde in a bioconversion system. The quantity of 2-hydroxymuconic semialdehyde metabolite accumulated is at least between about 0.1–1 gram per liter of bioconversion medium.

2-Hydroxymuconic Semialdehyde Production

Aromatic substrates that can be bioconverted to 2-hydroxymuconic semialdehyde and related metabolites include toluene, m-xylene, p-xylene, 4-ethyltoluene, 4-fluorotoluene, 4-methoxytoluene, mesitylene, benzyl alcohol, benzaldehyde, benzoic acid, catechol, 4-methylcatechol, and the like.

The rate of aromatic substrate (e.g., toluene or catechol) conversion with a constructed mutant microbial culture typically is at least about 100-200 milligrams of 2-hydroxymuconic semialdehyde produced per dry weight gram of cells per hour. The conversion of non-growth aromatic feedstock proceeds readily at a dry weight cell concentration between about 1-50 grams per liter, with a resultant 2-hydroxymuconic semialdehyde production rate of at least about 100-200 milligrams per liter per hour.

Under optimal conditions, the 2-hydroxymuconic semialdehyde accumulation limit can approach up to about one gram of 2-hydroxymuconic semialdehyde per liter of bioconversion medium. The microbiological oxidation process normally is conducted at ambient temperatures up to about 31° C.

The 2-hydroxymuconic semialdehyde metabolite can be recovered from the bioconversion medium by conventional means, such as by extraction of the acidified aqueous medium with an organic solvent after the cells have been removed.

The 2-hydroxymuconic semialdehyde metabolite also can be derivatized in the bioconversion medium, e.g., in order to form a stable derivative and/or to facilitate recovery of the metabolite.

It is particularly advantageous to conduct a present invention bioconversion process in the presence of a bisulfite salt. As illustrated in Example III, the addition of sodium bisulfite ($NaHSO_3$) to a culture medium causes the sequestering of 2-hydroxymuconic semialdehyde in the form of an adduct between the bisulfite and aldehyde functionalities. The formation of an adduct has the effect of reducing the toxicity of 2-hydroxymuconic semialdehyde to the culture microorganism, and of enhancing the accumulation level of the 2-hydroxymuconic semialdehyde as the bisulfite adduct in the culture medium.

It is further advantageous to conduct the bioconversion process under nutrient limited conditions to achieve a higher accumulated yield of 2-hydroxymuconic semialdehyde, whereby the microbial population is stabilized by the prevention of a growth advantage for revertants which are capable of growing on the aromatic substrate (e.g., toluene). These conditions can be accomplished by limiting the supply of nitrogen and/or phosphorus to the bioconversion medium.

The following examples are further illustrative of the present invention. The components and specific ingredients are presented as being typical, and various modifications can be derived in view of the foregoing disclosure within the scope of the invention.

EXAMPLE I

This Example illustrates the isolation of toluene oxidizing microorganisms as described in U.S. Pat. No. 4,355,107.

Soil samples were collected from a variety of areas and added to medium plus paraffin containing toluene. After shaking at 28° C. for 24 hours growth was apparent in the medium. Strains were isolated by streaking on agar plates containing a vial of toluene in the lid. Colonies appeared on the agar after approximately 36 hours. The size of these colonies ranged from 1 to 5 mm. A representative sampling of these colonies was taken and cultures were stored under liquid nitrogen for long-term preservation.

A strain derived from one of the largest colonies was chosen for further work and designated MW 1000. This strain was identified as a *Pseudomonas putida* Biotype A on the basis of the following criteria:

(a) the cells were rod shaped, vigorously motile and polarly flagellated;
(b) cells grew well on benzoate and p-hydroxybenzoate;
(c) cell growth on benzoate induced the synthesis of carboxymuconate lactonizing enzyme and carboxymuconolactone decarboxylase but not protocatechuate oxygenase, a pattern of regulation characteristic only of the *Pseudomonas putida* Biotype A;
(d) the induced enzymes muconolactone isomerase, carboxy-muconate lactonizing enzyme, and carboxy-muconolactone decarboxylase were immunologically identical with those enzymes synthesized by *Pseudomonas putida* Biotype A, a saprophytic organism extensively studied in the literature.

A growth study of MW 1000 on toluene was conducted and it was found that the organism grew with a doubling time of approximately 3.5 hours and had a 5 hour lag period. Toluene grown MW 1000 consumed oxygen when presented with toluene, benzyl alcohol, benzaldehyde, m-toluate or catechol. With catechol the medium turned yellow indicating the production of excess 2-hydroxymuconic semialdehyde.

The presence of the meta pathway was confirmed by demonstration of 2,3-oxygenase activity in cell free extracts and a failure to demonstrate the 1,2-oxygenase even after inactivation of the 2,3-oxygenase by treatment with hydrogen peroxide. MW 1000 also oxidized benzoate via the meta pathway following induction with benzoate.

MW 1200 is a mutant of MW 1000 which is constitutive for toluate oxidation. It is obtained by growing MW 1000 in enrichment cycles on m-toluate. MW 1200 exhibits a higher catechol 2,3-oxygenase activity than MW 1000.

EXAMPLE II

This Example illustrates the construction of a *Pseudomonas putida* Biotype A strain ATCC No. 39213 type mutant which is capable of oxidizing toluene to accumulated 2-hydroxymuconic semialdehyde (HMSA) via the meta (catechol 2,3-oxygenase) pathway.

The starting microorganism is the *Pseudomonas putida* Biotype A mutant strain MW 1200 described in Example I.

Strain MW 1200 is subjected to 60 generations of growth on benzoate which selects for loss of the TOL plasmid. The "cured" strain isolated by this procedure metabolizes benzoate via the chromosomal ortho pathway rather than the plasmid meta pathway, and no longer grows on toluene, p-xylene, m-xylene, p-toluate or m-toluate. This strain is designated BAC and its streptomycin derivative is designated BACS.

BACS is mutagenized with N-methyl-N'-nitrosoquanidine (NNG), selected against growth on benzoate with amoxicillin and D-cycloserine, and plated onto 5 mM benzoate plus 0.5 mM succinate. Small colonies on this media are tested for growth on benzoate and catechol. A mutant unable to grow on benzoate is shown by enzyme assay to be defective in muconate lactonizing enzyme (cat B) and designated BACS 2-4.

A TOL plasmid (pWWO) is transferred by conjugation from PaW15 (a leucine auxotroph) to BACS 2-4. A single colony of PaW15 is used to inoculate liquid NO media containing 1 mM leucine plus a vial of toluene, and is grown overnight. A single colony of BACS 2-4 from a nutrient agar plate is inoculated into Luria Broth and grown overnight. 5 ml of each overnight culture are mixed and filtered onto a presterilized Millipore filter (0.45 μm), placed on a nutrient agar plate and incubated overnight at 30° C. Controls consist of 5 ml samples of PaW15 and BACS 2-4 separately filtered and incubated overnight. The following day the filters are suspended in 50 ml of minimal media, diluted $10^{-2}$, $10^{-4}$, $10^{-6}$, and 0.1 ml aliquots are spread onto NO media agar plates containing 5 mM m-toluate plus 100 μg/ml streptomycin. All transconjugants demonstrate a coinheritance of all TOL plasmid encoded functions. A single colony is purified and designated BACS 2-4 (pWWO).

α-Hydroxymuconic semialdehyde (HMSA) can be metabolized by either the Xyl F gene encoded enzyme (HMSA hydrolase) or by the Xyl G gene encoded enzyme (HMSA dehydrogenase). However, the corresponding metabolite in m-xylene metabolism, 2-hydroxy-6-keto-2,4-heptadienoic acid, can only be metabolized via the Xyl F gene encoded enzyme (HMSA hydrolase), whereas Xyl G is inactive towards this substrate.

On this basis, BACS 2-4 (pWWO) is mutagenized with NNG, selected against growth on m-toluate by amoxicillin and D-cycloserine enrichments, and plated onto 5 mM m-toluate plus 0.5 mM succinate. Small colonies are selected and tested for the inability to grow on m-toluate. At least one mutant accumulates the methyl ketone ring fission product from m-toluate. When this type mutant is grown on Luria broth plus toluene and assayed for enzymes of the TOL plasmid, it is found to be defective in Xyl F (HMSA hydrolase), but still retains a functional Xyl G gene encoded enzyme (HMSA dehydrogenase). In addition, this type of mutant strain is able to grow on toluene, benzoate, p-xylene, p-toluate, but does not grow on m-xylene or m-toluate. The strain with inactive Xyl F encoded enzyme (HMSA hydrolase) is designated WG49.

Strain WG49 is mutagenized with NNG, selected against growth on p-toluate by enrichment with amoxicillin and D-cycloserine, and plated on nutrient agar plus 5 mM p-toluate. A single yellow colony is observed out of 400,000 colonies examined. This colony is purified and found unable to grow on toluene, benzoate, p-xylene, p-toluate, m-xylene or m-toluate. However, an accumulation of a yellow metabolite is observed when the above substrates are supplemented in nutrient agar. When this mutant strain is grown on Luria broth plus toluene and assayed for enzymes of the TOL plasmid, it is found to be inactive in both the Xyl F encoded enzyme (HMSA hydrolase) and the Xyl G encoded enzyme (HMSA dehydrogenase), but retains an active Xyl E encoded enzyme (catechol 2,3-oxygenase). This strain is designated WG49.2 and had the genotype of cat B⁻ (pWWO Xyl F⁻ Xyl G⁻) Sm'.

A WG49.2 type of mutant strain has been accorded accession ATCC No. 39213.

EXAMPLE III

This Example illustrates the bioconversion of an aromatic substrate to an accumulated quantity of 2-hydroxymuconic semialdehyde with a microorganism of the type constructed in Example II. A colony of strain WG49.2 from a nutrient agar plate is inoculated into 50 ml of NO medium containing 20 mM glucose and grown overnight. A 20 ml portion of this overnight culture is used to inoculate a 1750 ml fermentor containing a modified NO medium with 4.25 mM ammonium sulfate, 20 mM glucose and 0.1% antifoam. After growth to stationery phase due to nitrogen limitation (250-300 klett units), toluene is introduced by sparging liquid toluene with air at 0.3 cubic feet per hour.

Under both batch and continuous conditions, a transient accumulation of up to about 1.8 mM of 2-hydroxymuconic aldehyde is observed. The rate of 2-hydroxymuconic semialdehyde production observed is in the range between about 100-200 milligrams per liter of bioconversion medium per hour.

When a neutralized solution of sodium metabisulfite is added to a bioconversion system as described above, an accumulation of up to about 7.8 mM of 2-hydroxymuconic semialdehyde-bisulfite adduct is obtained (as in Figure).

The adduct is a stable compound under neutral pH conditions. Under alkaline pH conditions (e.g., by the addition of sodium hydroxide), the adduct decomposes to yield the 2-hydroxymuconic semialdehyde content of the adduct in a free form.

If the adduct solution is treated with ammonium ions, then the product obtained is picolinic acid.

Picolinic acid or substituted picolinic acid is decarboxylated readily to the corresponding pyridine derivatives, employing reaction conditions such as those described in the Canadian Journal of Chemistry, 50, 3017(1972) publication by G. E. Dunn et al.

Similar bioconversion to 2-hydroxymuconic semialdehyde is observed when the aromatic substrate is m-xylene, p-xylene, benzoic acid or catechol in the invention process.

What is claimed is:

1. A process for the production of 2-hydroxymuconic semialdehyde or substituted 2-hydroxymuconic semialdehyde comprising
   (1) Reacting toluene or substituted toluene with a Pseudomonad bacterial culture in the presence of molecular oxygen, said bacterial culture exhibiting catechol 2,3-oxygenase activity that is not inhibited in the presence of less than about 0.1 gram of 2-hydroxymuconic semialdehyde or substituted 2-hydroxymuconic semialdehyde per liter of bioconversion medium, and which exhibits no enzymatic activity that metabolizes 2-hydroxymuconic semialdehyde or substituted 2-hydroxymuconic semialdehyde
   (2) Allowing the 2-hydroxymuconic semialdehyde or substituted 2-hydroxymuconic semialdehyde to accumulate in the bioconversion medium
   (3) recovering the 2-hydroxymuconic semialdehyde or substituted 2-hydroxymuconic semialdehyde.

2. A process for the production of a 2-hydroxymuconic semialdehyde type metabolite which comprises reacting an aromatic hydrocarbon corresponding to the formula:

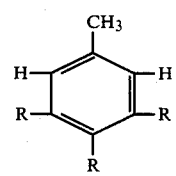

where R is hydrogen or an alkyl group containing between about 1-4 carbon atoms, with Pseodomonad bacterial culture in the presence of molecular oxygen, said culture exhibiting catechol 2,3-oxygenase activity that is not inhibited in the presence of less than about 0.1 gram of a 2-hydroxymuconic semialdehyde metabolite per liter of bioconversion medium, and which lacks active catechol 1,2-oxygenase, 2-hydroxymuconic semialdehyde hydrolase and 2-hydroxymuconic semialdehyde dehydrogenase, wherein the metabolite which is produced to the formulas:

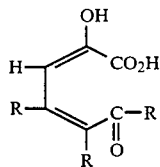

where R is as previously defined,
(3) Allowing said 2-hydroxymuconic semialdehyde type metabolite to accumulate in the bioconversion medium, and
(4) Recovering said 2-hydroxymuconic semialdehyde product.

3. A process in accordance with claim 2 wherein the aromatic hydrocarbon is toluene.

4. A process in accordance with claim 2 wherein the aromatic hydrocarbon is m-xylene.

5. A process in accordance with claim 2 wherein the aromatic hydrocarbon is p-xylene.

6. A process in accordance with claim 2 wherein the bioconversion medium is buffered to provide a pH in the range between about 6-9.

7. A process in accordance with claim 2 wherein the reaction is conducted under nutrient limited conditions.

8. A process in accordance with claim 2 wherein the metabolite is accumulated in a quantity greater than about 0.1 gram per liter of bioconversion medium.

9. A process for the production and accumulation of 2-hydroxymuconic semialdehyde or substituted 2-hydroxymuconic semialdehyde which comprises (1) Reacting catechol or substituted catechol with a Pseudomonad bacterial culture in the presence of molecular oxygen, said culture exhibiting catechol 2,3-oxygenase activity that is not inhibited in the presence of less than about 0.1 gram of 2-hydroxymuconic semialdehyde or substituted 2-hydroxymuconic semialdehyde per liter of bioconversion medium, and which exhibits no enyzmatic activity that metabolizes 2-hydroxymuconic semialdehyde or substitute 2-hydroxymuconic semialdehyde,
(2) Allowing said 2-hydroxymuconic semialkehyde or substituted 2-hydroxymuconic semialdehyde to accumulate, and
(3) recovering the 2-hydroxymuconic semialdehyde or substituted 2-hydroxymuconic semialdehyde.

10. A process in accordance with claim 9 wherein the catechol is substituted with one or more alkyl groups.

11. A process in accordance with claim 9 wherein the Pseudomonad culture is ATTC No. 39213 strain of *Pseudomonas putida* Biotype A.

12. A process in accordance with claim 9 wherein the bioconversion medium contains bisulfite ions.

* * * * *